United States Patent [19]

Tatsuno

[11] Patent Number: 4,595,291
[45] Date of Patent: Jun. 17, 1986

[54] PARTICLE DIAMETER MEASURING DEVICE

[75] Inventor: Kyoichi Tatsuno, Yokohama, Japan

[73] Assignee: Tokyo Shibaura Denki Kabushiki Kaisha, Kawasaki, Japan

[21] Appl. No.: 541,023

[22] Filed: Oct. 12, 1983

[30] Foreign Application Priority Data

Oct. 15, 1982 [JP] Japan .................. 57-179739
Mar. 25, 1983 [JP] Japan .................. 58-49923

[51] Int. Cl.⁴ .......................... G01N 15/02
[52] U.S. Cl. ..................... 356/336; 356/343
[58] Field of Search ............ 252/227; 340/630; 356/336, 343, 438, 439, 441, 442, 446

[56] References Cited

U.S. PATENT DOCUMENTS

| | | | |
|---|---|---|---|
| 3,549,264 | 12/1970 | Christie | 356/446 |
| 4,146,799 | 3/1979 | Pitt et al. | 356/343 |
| 4,192,613 | 3/1980 | Hammar | 356/386 |
| 4,265,535 | 5/1981 | Pitt | 356/343 |
| 4,265,538 | 5/1981 | Wertheimer | 356/343 |
| 4,497,577 | 2/1985 | Sato et al. | 356/336 |

OTHER PUBLICATIONS

AIAA Paper No. 76-69, A Laser Diagnostic Technique for the Measurement of Droplet and Particle Size Distribution, 1976.
The 1st International Conference on Liquid Atomization and Spray Systems, A Light Scattering Technique for Determining Droplet Size Distributions in Two-Phase Liquid-Dominated Nozzle Jets, Alger et al., (1978).

Primary Examiner—R. A. Rosenberger
Attorney, Agent, or Firm—Oblon, Fisher, Spivak, McClelland & Maier

[57] ABSTRACT

A particle diameter measuring device for measuring the particle diameter distribution of a number of particles to be measured, wherein a laser beam guided through a radiating optical fiber is re-formed by collimator lenses into parallel beams having an adequate diameter and is then irradiated onto the particles to be measured; a plurality of optical fibers are arranged along a circle whose center is a point P located in the particles, the receiving end of any of the optical fibers being directed toward point P. The optical fibers receiving the scattered light are arranged close to one another in the range of small scattering angles, while they are roughly arranged in the range of large scattering angles. A transmitted light enters into that optical fiber which is so arranged as to coincide with the laser beam incident direction, the intensity of this transmitted light being detected by a photodetector. Light scattered at various angles, which angles are formed with reference to the laser beam incident direction, is received by the other optical fibers, their intensities being detected by the other photo-detectors. The transmission factor $t = I_{out}/I_{in}$ is calculated from the intensity of the transmitted light. The particle diameter distribution $n(D)$ is calculated in the form of relative values, using the angular distribution $I(\theta)$ of the scattered light intensity. The particle diameter distribution $N(D)$ is calculated in the form of absolute values, using $t$, $n(D)$ and light pass length $L$. On the while, particle diameter distribution $N(D)$ or $n(D)$ can be measured with high accuracy, independently of the diameter of the particles. Since it is easy to measure the scattered light intensities in a range of scattering angles from 0° to 30°, the particle diameter distribution of particles, the diameter thereof are smaller than 0.1 μm, can be obtained.

18 Claims, 17 Drawing Figures

PARTICLE DIAMETER MEASURING DEVICE

BACKGROUND OF THE INVENTION

The present invention relates to a device for measuring the diameters of particles.

A number of well known devices have been used in carrying out the so-called forward scattering method of measuring the diameters of particles, such drops of liquid in the turbine (the diameter of each of drops being from 0.1 to 10 μm) and drops of fuel which are jet-sprayed into the combustion means (the diameter of each of drop being from 2 to 200 μm).

Particle diameter measurement according to the forward scattering method is based on the following principle. Where parallel beams of mono-chromatic light, such as laser beams, are irradiated onto a spherical particle whose diameter is D, the light intensity scattered by one particle in a direction which makes an angle $\theta$ in relation to the incident direction of the beam can be calculated accurately, based on the Mie scattering theory. On the other hand, where laser beams are irradiated onto a number of particles, the measured light intensity $I(\theta)$ scattered by many particles to the angle $\theta$ is expressed by the following equation (1):

$$I(\theta) = \int i(D,\theta) \cdot n(D) dD \tag{1}$$

wherein n(D) represents the density of particles whose diameter is D. When the light intensity scattered by a number of particles is measured at various angles $\theta$ to obtain the angular distribusion $I(\theta)$ of scattered light intensity, the particle diameter distribution n(D) can be calculated from this distribution $I(\theta)$, employing equation (1).

Figure 1:
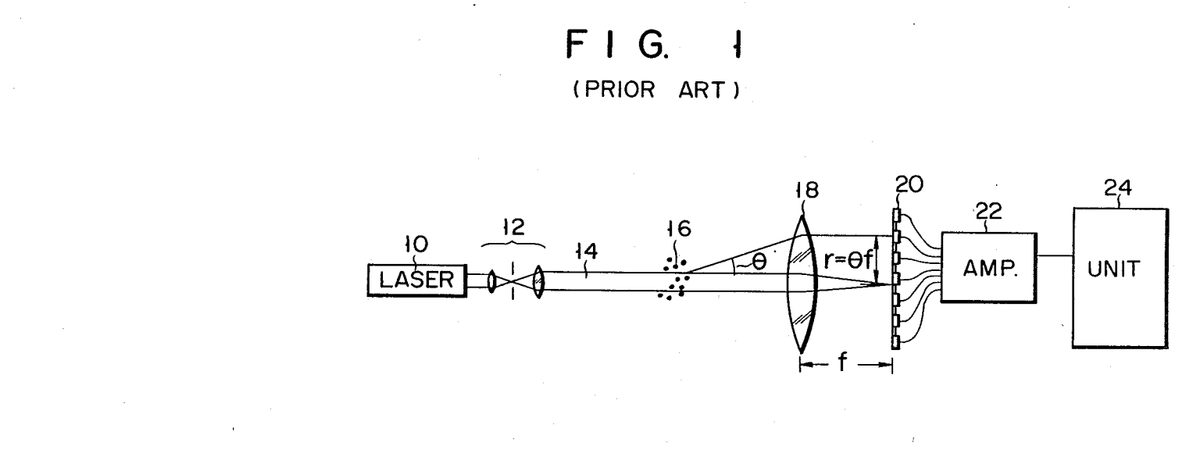
FIG. 1 is a sketch of a conventional particle diameter measuring device.

FIG. 1 shows a conventional particle diameter measuring device designed to carry out the forward scattering method. Laser beams 14 emitted from a laser 10 pass-through collimater lenses 12 to become parallel beams having an adequate diameter, which are then irradiated onto a group of particles 16 to be measured, and are scattered by these particles. A photo-detector array 20 is separated only by the focusing distance f of a collecting lens 18 therefrom. Scattered light are received by the photo-detector array 20 through the collecting lens 18. The photo-detector array 20 comprises a plurality of ring-shaped photosensitive elements arranged concentrically on a face. The light scattered at angle $\theta$ is received by a photosensitive element whose radius is $r(=\theta f)$, and its light intensity is converted into an electric signal. Signals detected by the photo-detector array 20 are amplified by an amplifier 22 and are then fed to an arithmetic unit 24, where the particle diameter distribution n(D) is calculated from equation (1), using the angular distribution of scattered light intensity $I(\theta)$ detected by the photo-detector array 20.

Figure 2:
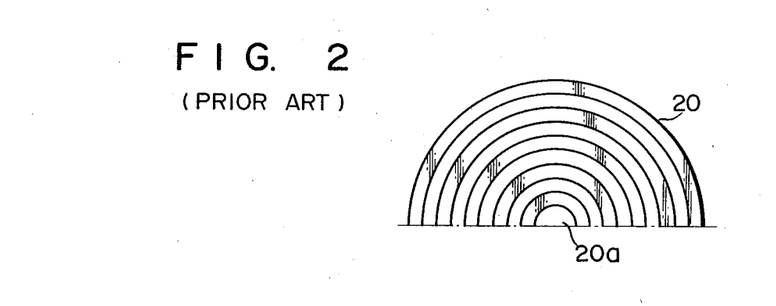
FIG. 2 is a front view of a photo-detector array.
Figure 3:
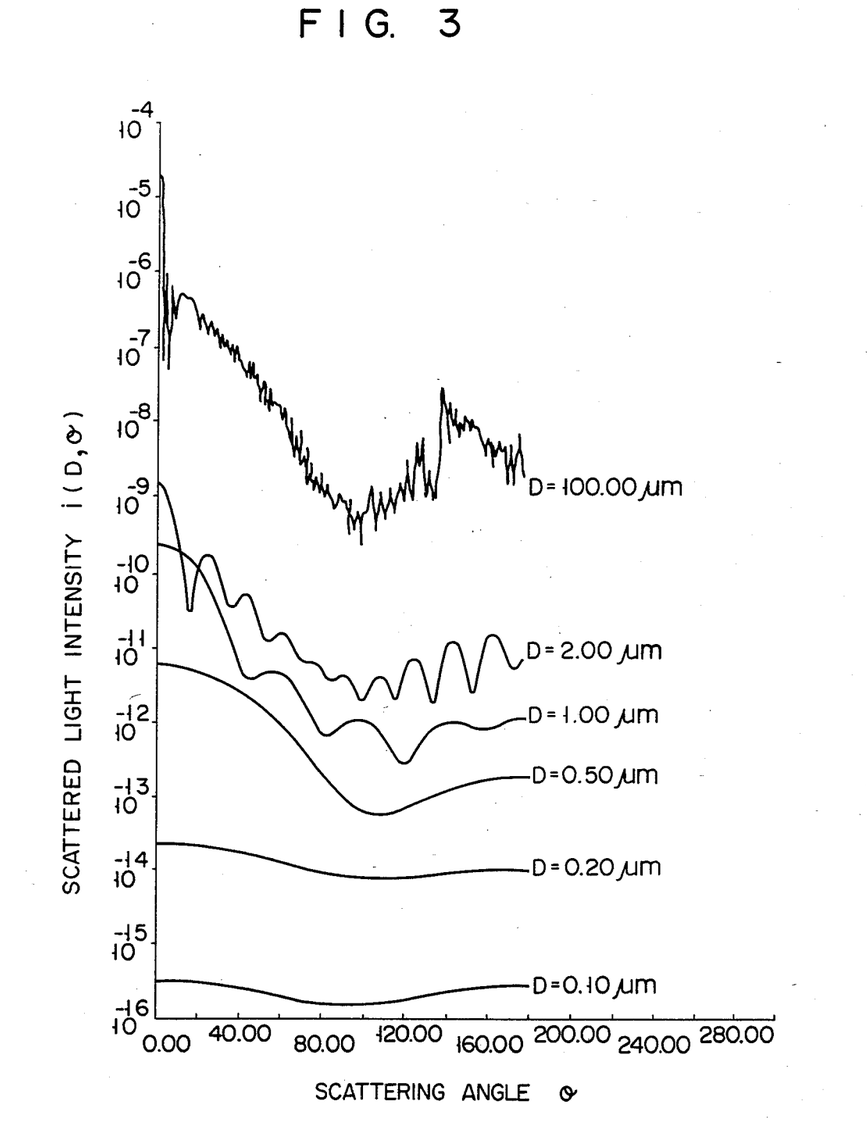
FIG. 3 is a graph showing the distribution pattern of the light intensity $i(D,\theta)$ scattered by one particle.

The conventional device, however, cannot measure scattered light intensity in a wide angle range, because the maximum aperture and minimum focal length for the collecting lens 18 are limited. The measuring range of the angle distribution $I(\theta)$ of scattered light intensity conducted by the conventional device is thus limited to the range from 0 to about 15°. FIG. 3 shows the light intensity $i(D,\theta)$ scattered by each of the particles whose diameters D are 0.10, 0.20, 0.50, 1.00, 2.00 and/or 100.00 μm. In the case of large-diameter particles, the distribution patterns of the light intensity $i(D,\theta)$ scattered by the particle may be distinguishable, even if the range of the measuring angles of the angular distribution $I(\theta)$ of scattered light intensity is narrow. Therefore, the particle diameter distribution n(D) can be obtained from the results of the narrow angular distribution $I(\theta)$ measurements. In the case of small-diameter particles, however, it is necessary to measure the angular distribution $I(\theta)$ of scattered light intensity over a wide range of scattering angles to distinguish the light intensity distribution scattered by the particle of a specified diameter and that scattered by the particles of other diameters, since the period of which the light intensity $i(D,\theta)$ scattered by the particle changes in relation to the scattering angle $\theta$ is long. Therefore, the conventional device can not obtain the particle diameter distribution n(D) of small-diameter particles, particularly particles whose diameters D are smaller than 1 μm. In addition, since high intensity transmitted light is irradiated onto a central portion 20a of the photo-detector array 20, high current is yielded in the central portion 20a and leaks to the circumferential ring-shaped photosensitive elements, to cause errors in the measurement of the angular distribution $I(\theta)$ of the scattered light intensity.

SUMMARY OF THE INVENTION

An object of the present invention is to provide a particle diameter measuring device capable of measuring the light scattered intensity in a wide range of scattering angles, to thereby obtain the particle diameter distribution of small-diameter particles.

Another object of the present invention is to provide a particle diameter measuring device capable of measuring the light intensity scattered at small angles, with high resolution, to thereby obtain the particle diameter distribution of large-diameter particles.

A further object of the present invention is to provide a particle diameter measuring device capable of measuring the particle diameter distribution of particles whose diameters are in a wide range, without the device being cumbersome and complex.

According to the present invention, a particle diameter measuring device is provided, for measuring the particle diameter distribution of a number of particles which are to be measured. A laser beam means irradiates laser beams onto the particles to be measured. The scattered light is received by a plurality of optical fibers arranged at certain scattering angles. The scattered light which is guided by each of the optical fibers is detected by a photodetector and converted into an electric signal. An arithmetic means calculates particle diameter distribution, as relative values of particle densities, from the detected light intensity scattered at predetermined scattering angles.

According to the present invention, scattered light is guided through the optical fibers to the photo-detector. The scattered light intensity can thus be measured with high accuracy, as well as with reliability, even if their scattering angles are large. In addition, a scattered light guided through each of the optical fibers is not influenced by scattered light guided through the other optical fibers or by any of the transmitted light, so that its intensity at a certain scattering angle can be measured with great accuracy.

On the other hand, the optical fibers can be so arranged that light scattered at a very small scattering angle or a very large scattering angle may come into any of these optical fibers, thus enabling particle diameter distribution to be measured in a wide range of particle diameters, without increasing the number of optical fibers (or the number of photo-detectors). More specifically, particle diameter distributions can be measured with great accuracy by a compact device, in the case of small-diameter particles which need a wide measuring range of scattering angles; and, also, in the case of large-diameter particles which need high resolution measurement in a narrow range of scattering angles.

DETAILED DESCRIPTION OF THE PREFERRED EMBODIMENTS

Figure 4:
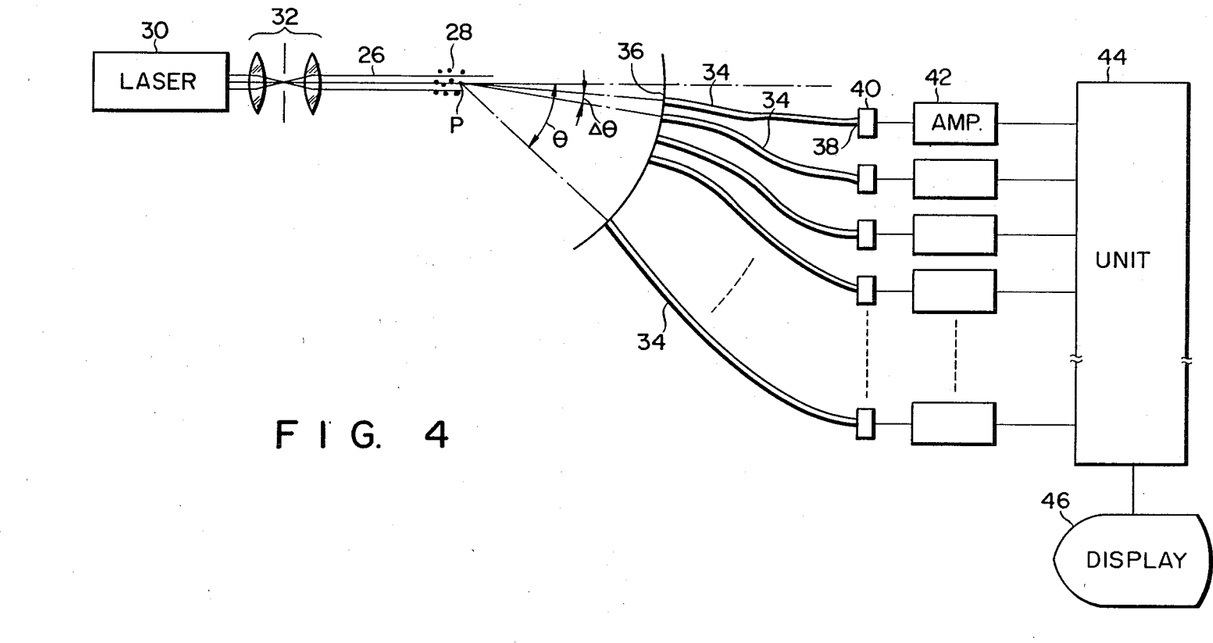
FIG. 4 is a view of a particle diameter measuring device according to a first embodiment of the present invention.
Figure 5:
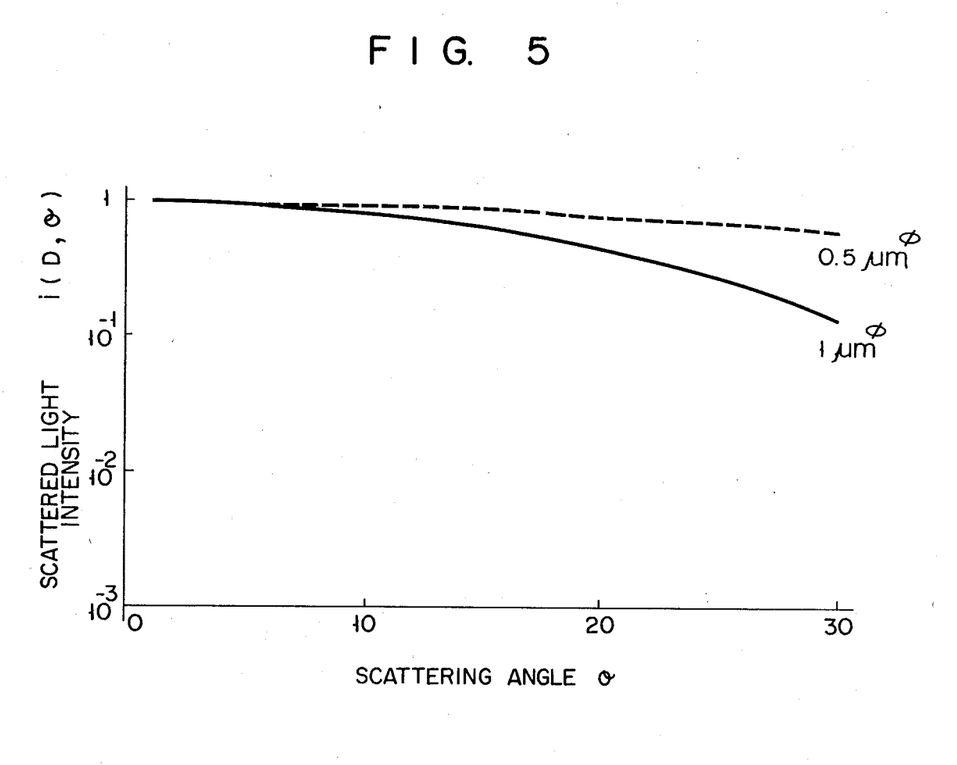
FIGS. 5 and 6 are graphs showing the calculated light intensity distribution scattered by uniform particles.

FIG. 4 shows an example of a particle diameter measuring device according to the present invention. Laser beams 26 are irradiated from a laser 30. Collimater lenses 32 are arranged on the optical axis of said laser beams 26 and make the laser beams 26 emitted from the laser 30 parallel beams with an adequate diameter. A number of particles 28 to be measured, which consists of a plurality of liquid drops, exists in a certain position on the optical axis of the laser beams 26. The laser beams 26 are irradiated onto and scattered by the particles 28. A plurality of (or n-numbered) optical fibers 34 are radially arranged on a face in front of the particles 28 when viewed from the incident direction of the laser beam. Receiving ends 36 of the optical fibers 34 are located on a circle which is drawn taking as its center a point P set within the particles 28, and any of optical axes (or scattering angle) of the optical fibers 34 is directed to the point P. The angle made between the optical axes of the adjacent optical fibers 34 is a certain angle $\Delta\theta$. A photo-detector 40 is arranged at a output end 38 of each of the optical fibers 34 and serves to detect the light guided through the optical fiber 34 and to convert it into an electric signal. The output of each of the photo-detectors 40 is amplified by an amplifier 42 and is then fed to an arithmetic unit 44, which calculates the particle diameter distributions n(D), using the angular distributions $I(\theta)$ of scattered light intensity detected by the photo-detectors 40, i.e., by using the measured light intensity $I(\Delta\theta)$, $I(2\Delta\theta)$, $I(3\Delta\theta)$, ..., $I(n\Delta\theta)$ at the scattering angles $\Delta\theta$, $2\Delta\theta$, $3\Delta\theta$, ..., $n\Delta\theta$, and by employing equation (1). These particle diameter distributions n(D) are displayed on a display 46 connected to the arithmetic unit 44.

A micro-lens may be arranged to be located between the receiving end 36 of each of the optical fibers 34 and point P, to allow only the light parallel to the optical axis of the micro-lens, namely to the optical axis of the optical fiber 34, to enter the optical fiber 34. It may also be so arranged that a filter which allows only the light having the wavelength of the laser beams to pass therethrough is located between the output end 38 of the optical fiber 34 and the photo-detector 40, to remove stray light and keep them from being detected by the photo-detector 40.

According to the device constructed as described above, the optical fibers 34 are radially arranged, directing any of their optical axes toward point P. Even in the case of a light scattered at a large scattering angle $\theta$, therefore, it can be surely guided through the optical fiber 34 to the photo-detector 40, by which its intensity can be detected. In addition, the intensity of scattered light entered into each of the optical fibers 34 and detected by its corresponding photo-detector 40 is influenced neither by scattered light entering into the other optical fibers 34 nor by transmitted light not scattered by the particles 28 but passing straight ahead. Therefore, the angular distribution $I(\theta)$ of the scattered light can be detected with great accuracy by the photo-detectors 40. When the angle $\Delta\theta$ made between the optical axes of the adjacent optical fibers 34 is small, the particle diameter distribution n(D) of large-diameter particles, in which the changing period of the scattered light intensity with the scattering angle $\theta$ is short, can be measured with great accuracy.

Figure 6:
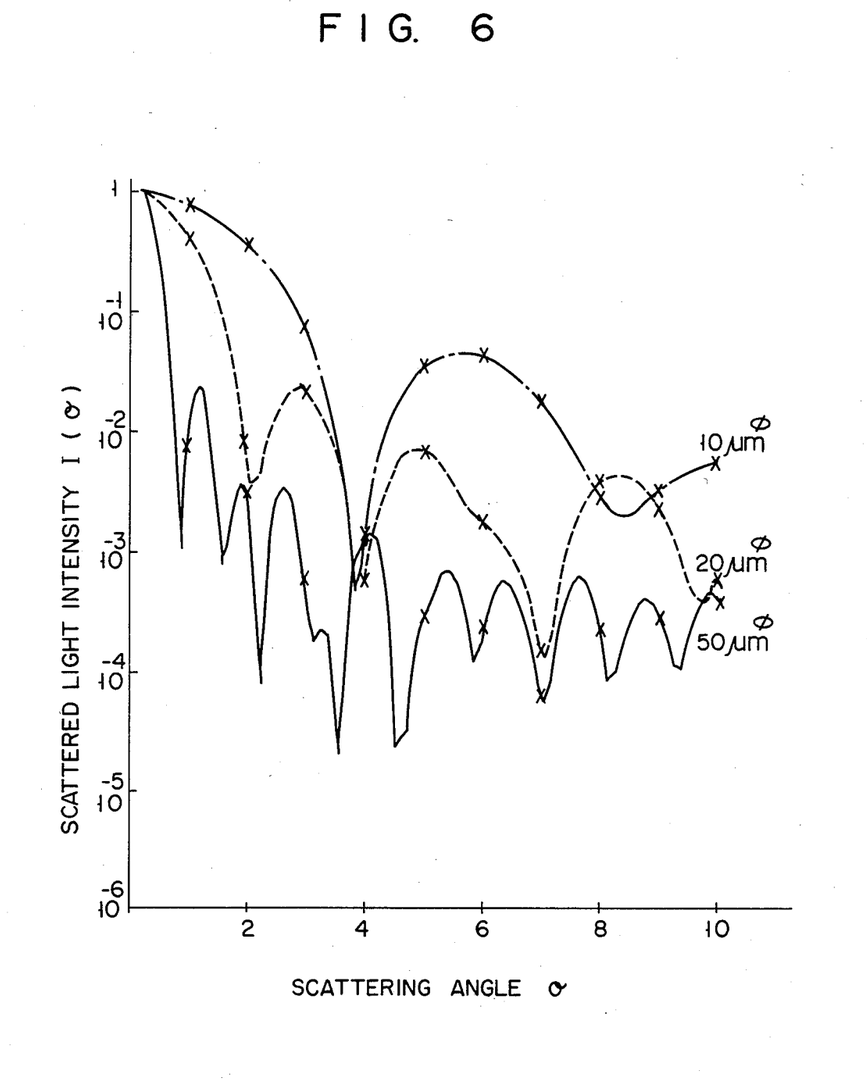

The present device enables the angular distribution $I(\theta)$ of scattered light to be measured in a wide range of from 0 to 30°. Therefore, even in the case of small-diameter particles (where $D = 1$ μm and 0.5 μm), which make the light intensity $i(D,\theta)$ scattered by a particle change, as shown in FIG. 6; with the scattering angle $\theta$, the difference in the patterns of the light intensity $i(D,\theta)$ can be distinguished. So the difference in the diameters D of such particles can be clearly recognized by measuring the angular distribution $I(\theta)$ of the light intensity, thus allowing their particle diameter distribution n(D) to be measured with great accuracy.

The angular distribution $I(\theta)$ of scattered light by each of the particles whose diameters D are 10, 20 and 50 μm were theoretically found over the scattering angle $\theta$ and are shown by a dot-and-chain line, broken line and solid line, respectively, in FIG. 6. If the light intensity scattered by each of the particles whose diameters D and 10, 20 and 50 μm, respectively are measured by setting the angle $\Delta\theta$ at 1°, the imaginary measured points are shown by marks x in FIG. 6. As may be seen from FIG. 6, the change of the scattered light intensity in relation to the scattering angle $\theta$ can be expressed with high accuracy, by smoothly connecting the measured points of the intensity, where the particle diameter D is 10 or 20 $\mu$m. The particle diameter distribution n(D) of particles which have diameters such as 10 $\mu$m and 20 $\mu$m can be thus measured with great accuracy. However, where the particle diameter D is 50 $\mu$m, for example, the changing period of the scattered light intensity in relation to the scattering angle $\theta$ is short, thus making it impossible to find the state of the change of the intensity i(D,$\theta$) from the results of the measured light intensity I($\theta$). It is therefore impossible to measure the particle diameter distribution n(D) of large-diameter particles (d=50 $\mu$m) when the angle $\Delta\theta$ made between the optical axes of the adjacent optical filers is set at 1°. Accordingly, it becomes necessary to set the angle $\Delta\theta$ smaller when the particle diameter distribution of large-diameter particles is to be measured.

In short, the range of scattering angles to be measured must be made wide when small-diameter particles are to be measured, while measuring points must be finely set in a small range of scattering angles when large-diameter particles are to be measured. When a device is an attempt to meet this need, it must be provided with an extremely large number of optical fibers and photo-detectors, thus becoming cumbersome, as well as complex in its signal processing line.

Figures 7, 8:
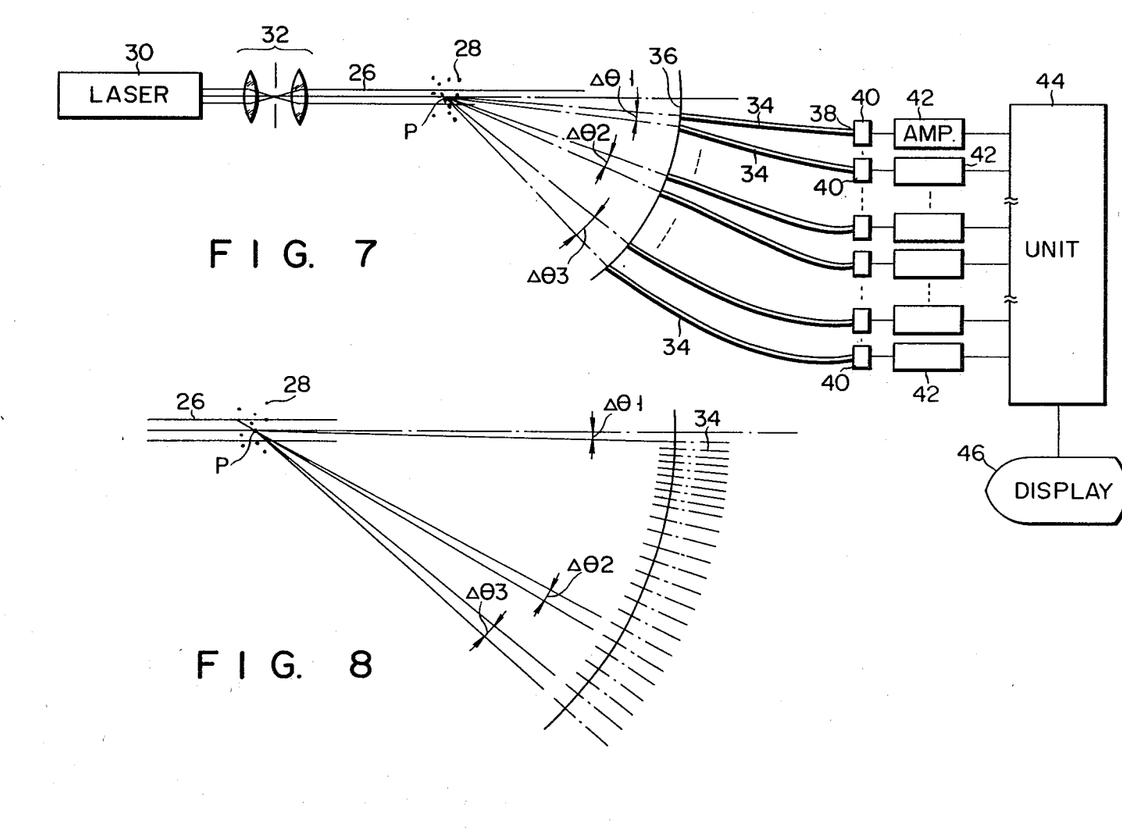
FIG. 7 is a view of another particle diameter measuring device according to a second embodiment of the present invention.
FIG. 8 is an enlarged view of an arrangement of optical fibers.

FIG. 7 shows another embodiment of a particle diameter measuring device according to the present invention, which embodiment is intended to eliminate the above-mentioned drawback. This embodiment shown in FIG. 7 is different from the one shown in FIG. 4 in the arrangement of optical fibers. Since the same parts shown in FIG. 4 are represented by the same numerals, a description of these parts will be omitted here. A plurality of optical fibers 34 are radially arranged on a circle whose center is a point P located in the particles 28, and any of the optical axes (or beam incoming directions) of the optical fibers 34 is directed toward point P. With this embodiment, the angle made between the optical axes of the adjacent optical fibers 34 is small, in relation to those fibers used in detecting small scattering angles; while it is large in relation to those used in detecting large scattering angles. As shown in FIG. 8, in which the arrangement of the optical fibers is enlarged, for example, ten optical fibers are arranged with their difference $\Delta\theta_1$ being kept at 0.5° when the scattering angle is in a range of from 1° to 5.5°. When the scattering angle $\theta$ is in a range of from 6° to 20°, fifteen optical fibers are arranged keeping the difference $\Delta\theta_2$ equal to 1°. When the scattering angle $\theta$ is in a range of from 22° to 30°, five optical fibers are arranged keeping the difference $\Delta\theta_3$ equal to 2°. The angular distribution I($\theta$) of scattered light detected by the photo-detectors 40, through the optical fibers located at each range of the scattering angles, are fed to the arithmetic unit 44 to calculate particle diameters distribution n(D) of the particles 28.

Figure 9:
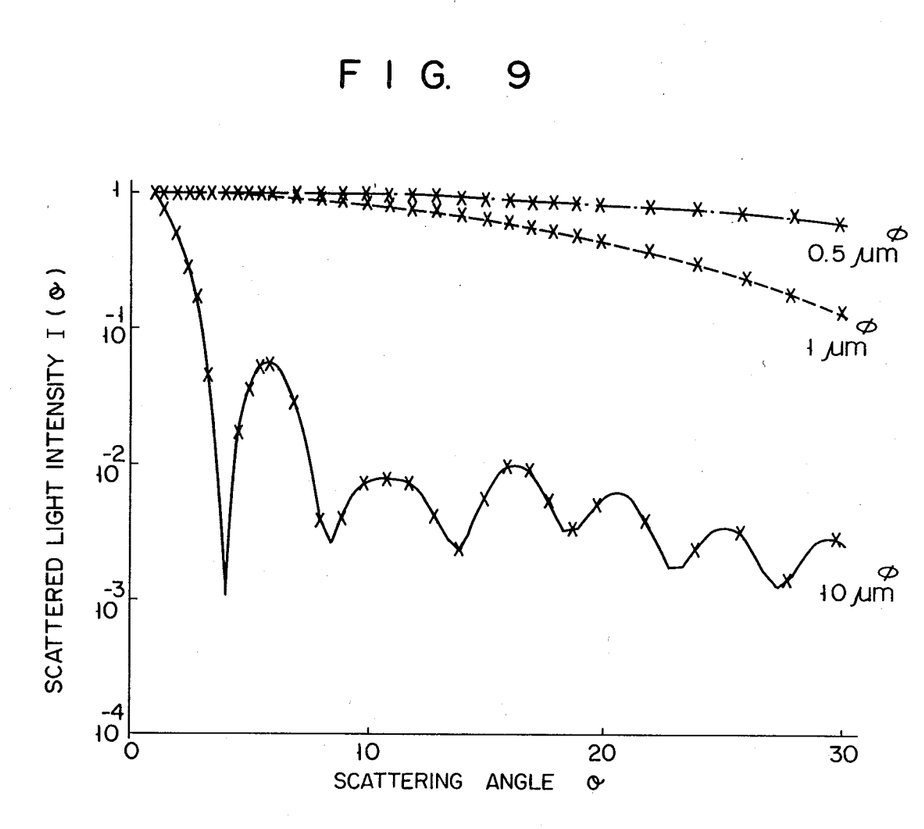
FIG. 9 is a graph showing the calculated light intensity pattern scattered from by uniform particles.

The angular distribution I($\theta$) of light scattered by each of the particles whose diameters D are 0.5, 1 and 10 $\mu$m were theoretically found over the scattering angle $\theta$ and are shown by a dot-and chain line, broken line and solid line, respectively, in FIG. 9. If the intensity of light scattered from each of the particles whose diameters D are 0.5, 1 and 10 $\mu$m, respectively, are measured by setting the difference $\Delta\theta_1$, $\Delta\theta_2$ and $\Delta\theta_3$ at 0.5°, 1° and 2° respectively, the imaginary measured points are shown by marks x in FIG. 9. As apparent from FIG. 9, each group of results measured is shown to distinctly, distinguish each of the scattered light intensity patterns in relation to the scattering angles $\theta$ even in both cases of small-diameter particles (D=0.5 and 1 $\mu$m) and large-diameter particles (D=10 $\mu$m). Therefore, the particle diameter distribution n(D) of particles which have a wide range of diameters, small and large, can be obtained from the measured values of the angular distribution I($\theta$) of light scattered by said particles. The total number of optical fibers used is 30, in this embodiment, which is same as that of them employed by the embodiment ($\Delta\theta=1$° and the range of the scattering angles is from 1° to 30°), as shown in FIG. 4. The particle diameter distribution n(D) can thus be measured over a wide range of particle diameters, without the device becoming cumbersome or its signal processing line being made complex.

It should be understood that the arrangement of the optical fibers is not limited to those employed by the above-described embodiments. The particle diameter distribution of each particles whose diameter is in a range of from 0.5 to 50 $\mu$m can be measured by arranging the optical fibers at the scattering angles of from 0° to about 30° to have above-mentioned differences interposed between the optical axes of the adjacent optical fibers. In case of measuring the particle diameter distribution of particles whose diameter is smaller than 0.5 $\mu$m, the optical fibers may be arranged at the scattering angles of from 0° to about 60°, with the difference $\Delta\theta$ kept in the range of from 2° to 4°. In case of measuring the particle diameter distribution of particles whose diameter is larger than 50 $\mu$m, the optical fibers may be arranged at the scattering angles $\theta$ of from 0° to 10°, keeping the difference $\Delta\theta$ in a range of from 0.1° to 0.5°. The difference $\Delta\theta$ may also be increased on a logarithmic scale as the scattering angle becomes larger, starting from zero. More specifically, the first optical fiber is located at a position where the scattering angle is 0.05°, and the others are then located, taking distance $\Delta\theta$ at 0.1°, 0.2°, 0.3°, 0.5°, 0.7°, 1.0°, 2.0°, 3.0°, 5.0°, 7.0°, 10.0°, . . . , successively. In sum, keeping the difference $\Delta\theta$ small, the optical fibers may be arranged in such a way as to measure the angular distribution of scattered light intensity with high resolusion, in the range of small scattering angles; while, keeping the difference $\Delta\theta$ large, they may also be arranged in such a way as to measure the angular distribution of scattered light intensity in the range of large scattering angles.

With the embodiments shown in FIGS. 4 and 7, since it is difficult to measure the absolute intensity of scattered light, the particle diameter distribution can be obtained with reference to only their relative values. In other words, the particle diameter distribution expressed in terms of the absolute values of the particles densities (numbers/cm$^3$) cannot be obtained.

Figure 10:
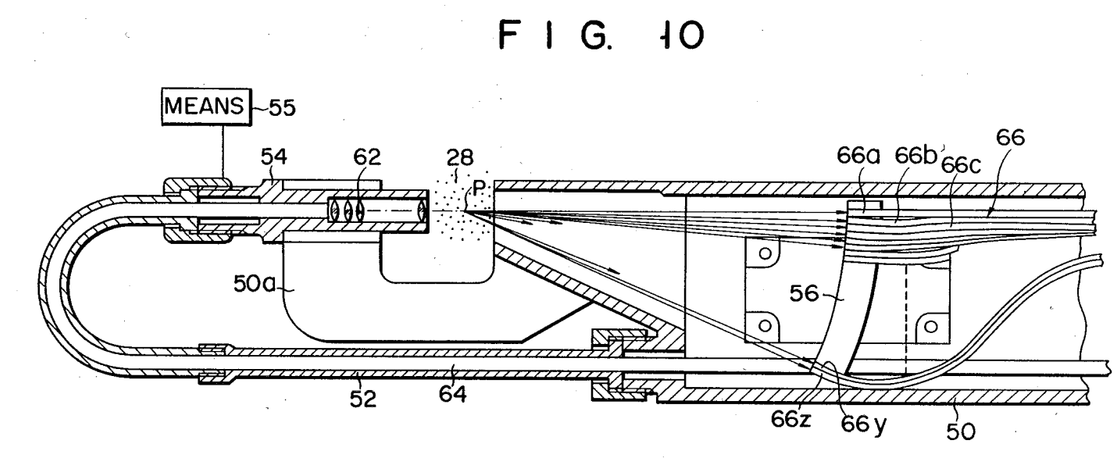
FIG. 10 is a sectional view of a particle diameter measuring device according to a third embodiment of the present invention.
Figure 12:
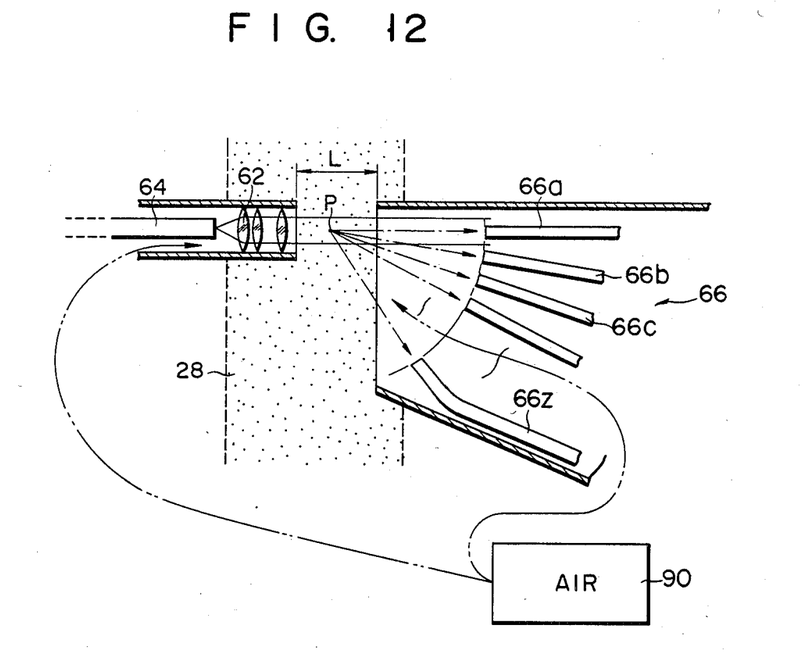
FIG. 12 is an enlarged view of the principal part of FIG. 10.

FIG. 10 shows a further embodiment of the particle diameter measuring device according to the present invention, which embodiment enables the particle diameter distribution expressed in terms of to be the absolute values of the particles densities (numbers/cm$^3$). This device is made flat as a whole and its particle diameter detecting portion is inserted into and between turbine blades, for example, to measure the diameter distribution of liquid drops inside the turbine. A body 50 has an inside hollow of flat shape and is made of stainless-steel or the like. A guide pipe 52 for laser beam radiation line is attached to the front end of the device body 50. The guide pipe 52 is curved in U-shape and a cylindrical laser beam radiating section 54 is attached to the front end of the guide pipe 52 in such a way that the section 54 can be reciprocated in relation to the guide pipe 52 by means of a driving means 55 such as micrometer mechanism. This section 54 is also supported by a support 50a extending from the front end of the device body 50. An optical fiber 64 for radiating laser beams, which is connected to a laser means or the laser 30 shown in FIGS. 4 and 7, for example, is housed inside both guide pipe 52 and section 54. A collimator lens 62 consisting of a group of lenses is housed inside the front half of the radiating section 54. As shown in FIG. 12, which shows an enlarged view of the circumference of the laser beams scattering section, the location of the particles 28 to be measured may be defined by purging air which flows as shown by the two dotted-chain line of FIG. 12. The purging air is supplied by an air generator 90.

Laser beams guided through the optical fiber 64 are re-formed by the collimator lens 62 into parallel beams having an adequate diameter, which are irradiated onto a number of particles 28, such as liquid drops, which are to be measured. The light pass length of laser beams passing through the particles 28, or light pass length L of scattering is thus defined by the purging air supplied by the air generator 90. This light pass length L of scattering can be set to any desired value by reciprocating the radiating section 54.

Figure 11:
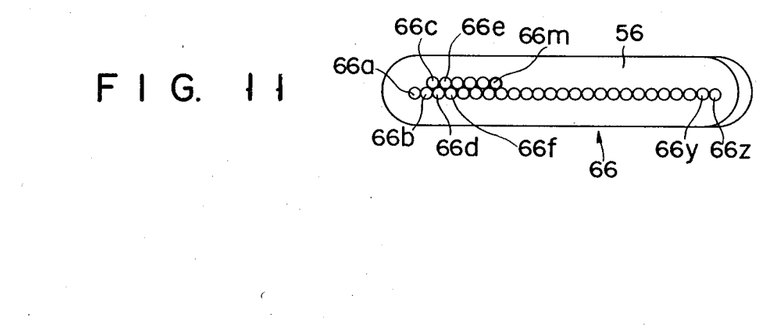
FIG. 11 is a side view of a group of optical fibers viewed from the incident direction of laser beam.

A group of optical fibers 66 is supported by a support 56 which is circularly curved in the widthwise direction of the device body 50. Similar to those employed by the embodiment of FIG. 7, the receiving ends of these optical fibers 66 are located on a circle whose center is a point P set on the light pass. The optical axis of each of the optical fibers 66 is directed toward point P. FIG. 11 is a side view of the group of optical fibers 66 when viewed from the incident side of the laser beams. As is apparent from FIGS. 10 and 11, the optical fiber 66a of the grouped ones 66 is so located as to coincide with the incident direction (or direction of the optical axis of the optical fiber 66) of laser beams radiated onto the group of particles 28. The beam not scattered by the particles 28 but passing straight therethrough comes into the optical fiber 66a. Twenty four optical fibers 66b, 66d, 66f, ..., 66y and 66z are arranged successively starting from the optical fiber 66a and in the width direction of the body 50. The angle difference between the optical fibers 66a and 66b is set so that the angle made between optical axes of both optical fibers taking the point P as its center becomes 1°, for example. Similarly, each of the differences between the optical fibers 66b and 66d, between 66d and 66f, ..., and between 66y and 66z is also set in such a way that the angle made between the optical axes of adjacent optical fibers, taking the point P as its center, becomes 1°, for example. On the other hand, six optical fibers 66c, 66e, ..., 66m are located between the optical fibers 66b and 66d, between 66d and 66f, ..., respectively, but shifted a little in the thickness direction of the support 56. Each of optical axes of the optical fibers 66b, 66e, ..., 66m is directed to the point P. Therefore, the optical axes of the optical fibers 66c, 66e, ..., 66m are a little slanted in relation to a face which is formed by the optical axes of the optical fibers 66a, 66b, 66d, 66f, ..., 66y and 66z. The angle made between the optical axis of optical fiber 66a and that of each of the optical fibers 66c, 66e, ..., 66m, taking point P as its center, is set at 1.5°, 2.5°, ..., 6.5°, respectively.

The light scattered intensity can thus be measured at every angle of 0.5°, in the range of the scattering angle from 1° to 7°, as well as at every angle of 1°, in the range of the scattering angle ranging from 7° to 24°. The receiving ends of the optical fibers 66a, 66b, ..., 66z are arranged closed together, to make the device compact. When optical fibers each having a diameter of 1 mm$^\phi$ are used in the device thus constructed, the distance between the point P and the optical fibers is about 60 mm. Each of the optical fibers 66 is lead to the back end of the body 50, and the scattered light guided through the optical fiber of the grouped ones 66 is converted by the photo-detector 40 (see FIG. 13) into an electric signal, said photodetector 40 being arranged at the back end of the body 50 and connected to the output end of each of the optical fibers 66. This signal is amplified by the amplifier 42 (see FIG. 13) and is then fed to an arithmetic unit 68, by which the particle diameter distribution expressed in terms of the absolute values can be calculated.

Figure 13:
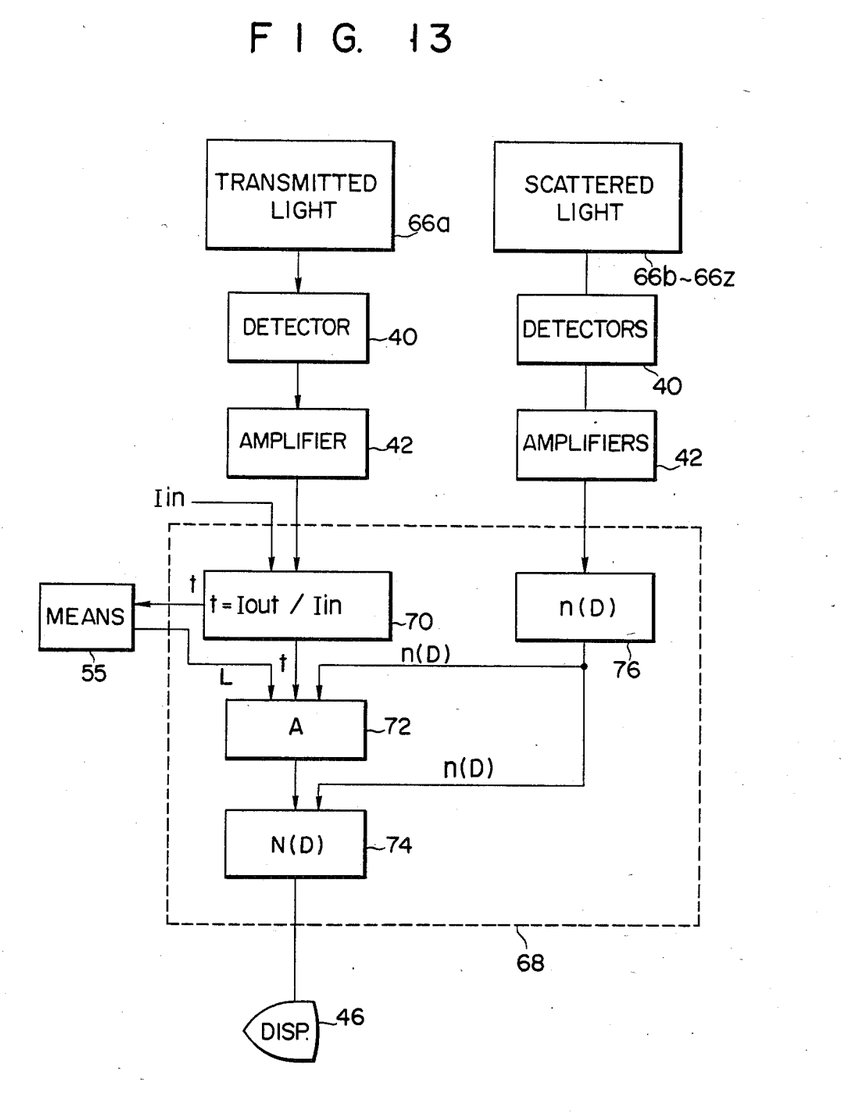
FIG. 13 is a block diagram of an arithmetic unit.

The arithmetic unit 68 which serves to calculate the particle diameter distribution may be described as a function of the transmission factor and scattered light detected by the device constructed described above, and with reference to the block diagram shown in FIG. 13. The transmitted (or pass-through) light is guided through the optical fiber 66a and is converted by the photo-detector 40 into an electric signal. This signal, which has been converted from the transmitted light whose intensity is Iout, is amplified by the amplifier 42 and is then fed to a calculator circuit 70 which serves to calculate the transmission factor (t=Iout/Iin). The intensity Iin of the incident laser beam, which is determined by the output of the laser 30 (see FIG. 7) and the like, is stored in the transmission factor calculating circuit 70. The transmission factor calculating circuit 70 calculates the transmission factor (t=Iout/Iin) by using the detected intensity Iout of the transmitted light and stored intensity Iin of the incident beam.

When the density of the particles density of the particles 28 is high, the number of particles by which laser beams are scattered or diffracted is large and multiple scattering caused by these particles is seen more frequently. In such a case, equation (1), or the relationship whereby the measured angular distribution I($\theta$) of the scattered light is expressed by superposing theoretically calculated intensity of the light scattered by one particle, will not exist. Measurement of the particle diameter distribution thus cannot be performed by the forward scattering method.

Figure 14:
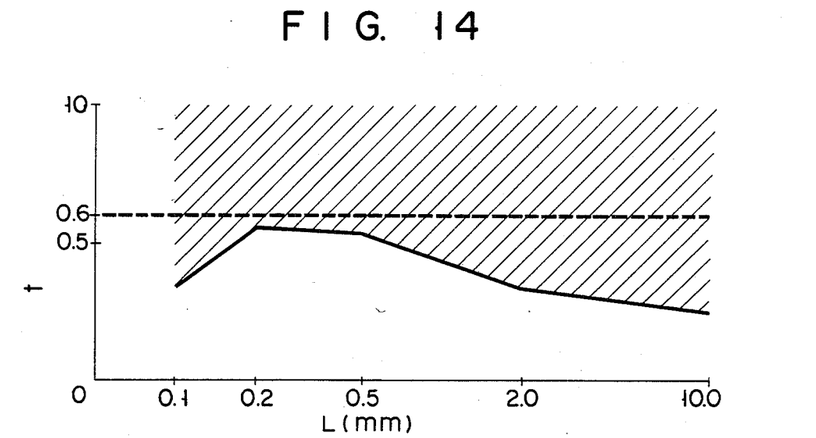
FIG. 14 is a graph showing, with oblique lines, the range of the transmission factor t, where particle diameter distribution can be measured without being influenced by multi-scattering.

FIG. 14 shows the obliquely-lined area of transmission factor t whereby measurement of the particle diameter distribution can be made without the influence of multiple scattering. Six kinds of particle diameters were selected in a range of from 0.312 to 11.9 mm, and six groups of polystyrene particles with selected diameters were suspended in water. The angular distribution of the scattered light was measured under such conditions. This measurement of the angular distribution of the scattered light intensity was carried out by varying the density of the particles in every group. The solid line in FIG. 14 shows the relationship between the transmission factor of particle groups and the light pass lengths L, wherein the angular distribution of the light scattered by particles of each group was measured in relation to specified light pass lengths L, successively lowering the density of particles in the group; wherein, when the measured results of the scattered light intensity distribution became coincident with a theoretically calculated intensity distribution, the transmission factor was measured in this time particle density; and, wherein the maximum transmission factor of measured transmission factors of particle groups thus was plotted in FIG. 14. It can be understood, therefore, that when the transmission factor is in the obliquely-lined area where the transmission factor is larger than the value expressed by the solid line, the particle diameter distribution can be measured in spite of any particle densities and diameters and without being influenced by multiple scattering. As shown by broken line in FIG. 14, multiple scattering causes no influence in spite of any light pass lengths L when transmission factor t is larger than 0.6. On the other hand, there exists an inverse proportion between logarithm log t of the transmission factor t and the light pass length L, as will be described later. Therefore, the transmission factor t can be adjusted by adjusting the light pass length L. When measured values of the transmission factor t are smaller than 0.6, they may be set larger than 0.6 by adjusting the light pass length L, in the case of this embodiment, so as to measure the angular distribution of the scattered light intensity.

The transmission factor calculating circuit 70 transmits the transmission factor t to the driver means 55 at the radiating section 54. When the transmission factor t is smaller than 0.6, the driver means 55 advances the radiating section 54, to shorten light pass length L, or to make the transmission factor t larger than 0.6. Light pass length L is given this case as a sum of moving length ΔL of the radiating section 54 caused by the driver means 55 and of light pass length $L_o$ at the time when the radiating section 54 is in its reference position, and applied from the driver means 55 to a calculator circuit 72 described later. The light pass length L fed to this calculator circuit 72 may be of any value from among those measured via the laser length measuring device, or micrometer.

On the other hand, scattered light received by the optical fibers 66b, 66c, . . . , 66z are converted by the photo-detectors 40 into electric signals, respectively. The signals detected corresponding to scattered light intensity are amplified by the amplifiers 42 and then fed to a calculator circuit 76 which serves to calculate particle diameter distribution n(D) expressed in terms of the relative values of particle densities. In short, the calculator circuit 76 calculates particle diameter distribution n(D) from angular distribution I(θ) of scattered light intensity, following equation (1).

$$I(\theta) = \int i(D,\theta) \cdot n(D) dD \tag{1}$$

This inversion from I(θ) to n(D) is concretely performed, by using the Logarithmic Constraint Inversion Method or the Logarithmic Distribution Function Approximation Method. The Logarithmic Distribution Function Approximation Method will be described here. By this method, the distribution parameters of n(D) are determined in such a way that the E value obtained from the following equation (2) becomes smallest.

$$E = |\log[I(\theta)] - \log[\int i(D,\theta)n(D)dD]|^2 \tag{2}$$

The distribution function of n(D) is assumed to be a normal distribution function, for example, which can be expressed by the following equation (3):

$$n(D) = \frac{1}{\sqrt{2} B} \exp\left[-\frac{(D-C)^2}{2B^2}\right] \tag{3}$$

wherein B and C represent distribution parameters. This normal distribution function is substituted, as an initial value, by equation (2) and corrected in such a manner of making E the smallest.

In the Logarithmic Constraint Inversion Method, the equation (1) is approximated by linear equations. Then, the particle diameter distribution n(D) is obtained by solving the linear equations under the following two conditions:

Condition (1): The distribution is smooth.
Condition (2): n≧0.

More precisely, Lagrange's method of undetermined multipliers is used to find the solution which satisfies condition (1), and the solution thus obtained is corrected to satisfies the Kuhn-Tucker theorem that characterizes the least squared solution under condition (2). The corrected solution is the particle diameter distribution n(D).

The particle diameter distribution n(D) expressed in terms of this relative values is fed from calculator circuit 76 to calculator circuit 72, which calculates a constant A. To the calculator circuit 72 are also fed transmission factor t=Iout/Iin from the calculator circuit 70 and light pass length L from the driver means 55. The calculator circuit 72 carries out operations using these data. In short, the transmission factor t=Iout/Iin passing through the group of particles 28 can be expressed by the following equation (4):

$$I_{out}/I_{in} = \exp\left\{-L \cdot \int_0^\infty C(D) \cdot N(D) d(D)\right\}, \tag{4}$$

wherein C(D) represents a sectional area in which beams scattering cross section of the particle with diameter D; and N(D), a particle diameter distribution expressed in terms of absolute values.

On the other hand, the following equation (5) is based on the relationship between particle diameter distribution n(D) expressed in terms of relative values and particle diameter distribution N(D) expressed in terms of absolute values:

$$N(D) = A \cdot n(D) \tag{5},$$

wherein A is a constant. When equation (4) is substituted by equation (5) and the logarithms of both sides are taken, the following relationship is obtained:

$$\ln(I_{out}/I_{in}) = -L \cdot A \int_0^\infty C(D) \cdot n(D) dD \tag{6}$$

C(D) has been obtained theoretically and n(D) has been measured as described above. In addition, A is constant. Therefore, there is the inverse proportional relationship between log t and L, as described above. On the other hand, the value of light pass length L has also been obtained. Therefore, constant A can be calculated from equation (6). The calculator circuit 72 calculates constant A from equation (6), using data as described above. The results thus calculated are fed to the calculator circuit 74, where particle diameter distribution N(D) expressed in terms of the absolute values of the densities of particles (numbers/cm³) is calculated.

The particle diameter distribution n(D) expressed in terms of relative values is also fed from calculator circuit 76 to calculator circuit 74, which calculates the particle diameter distribution N(D) expressed in terms of absolute values, using n(D) and constant A and the equation (5). This particle diameter distribution N(D) is displayed on the display 46.

This embodiment enables the particle diameter distribution expressed in terms of absolute values, which is extremely useful for the practical application. For example, wetness of steem in turbine is obtained from the particle diameter distribution expressed in terms of absolute value. In addition, light pass length L can be adjusted, corresponding to the measured value of the transmission factor, and the particle diameter distribution of any group of particles of all particle densities can be measured with great accuray, without the influence of multiple scattering.

Figure 15:
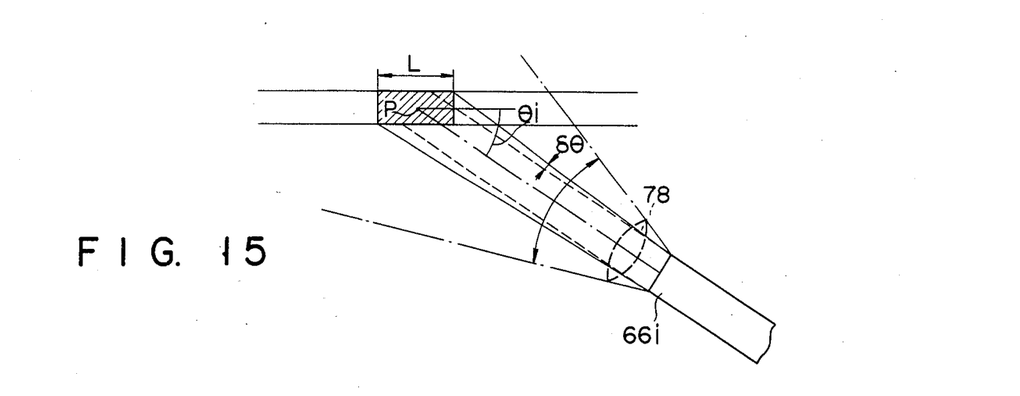
FIG. 15 is a view used in explaining an error in a scattering angle.

Light pass length L is usually set at 10 mm. The distance between a point P in FIG. 15 and a optical fiber 66i located at a specified scattering angle θi is about 60 mm, as already explained. The scattered light received by the optical fiber 66i only includes the light scattered at the range of from $\theta i - \delta\theta$ to $\theta i + \delta\theta$, wherein $\delta\theta$ is very small. Therefore angular distribution I(θ) of the scattered light intensity can be measured with great accuracy. Particularly in the case of the embodiment shown in FIG. 10, light pass length L can be adjusted in such a way that angular distribution I(θ) is not influenced by multiple scattering, and light straying outside the predetermined area where light is scattered is not received by the optical fiber 66i. It is therefore unnecessary that a collimator lens 78 be arranged adjacent to the receiving end of the optical fiber 66i, to shield the straying beams.

Figure 16:
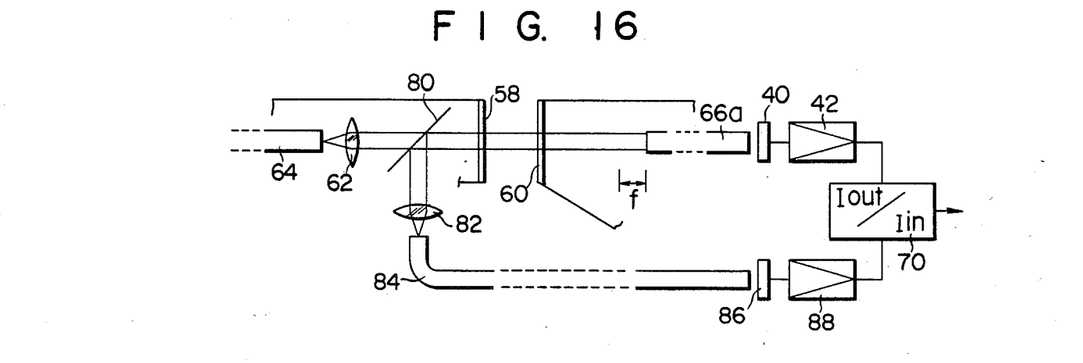
FIG. 16 is a view of a variation of the particle diameter measuring device according to the third embodiment.

As shown in FIG. 16, the intensity Iin of incident beams may be detected in such a way that a part of the radiated laser beam is split by a beam splitter 80, the split beam is guided through a collimator lens 82 and an optical fiber 84 to a photo-detector 86, and the intensity of the split beam is converted by the photodetector 86 into an electric signal. This signal converted from the intensity Iin of the incident beam is amplified by an amplifier 88, and is then fed to a calculator circuit 70 to be used in calculation of the transmission factor t. Any error in the transmission factor t caused by changes in the intensity of a radiated laser beam can be eliminated by using the practically measured value of the intensity Iin of the incident beam. Even if the intensity of a laser beam is unstable at the time of turning on the laser 30, the particle diameter distribution can thus be measured with great accuracy.

Figure 17:
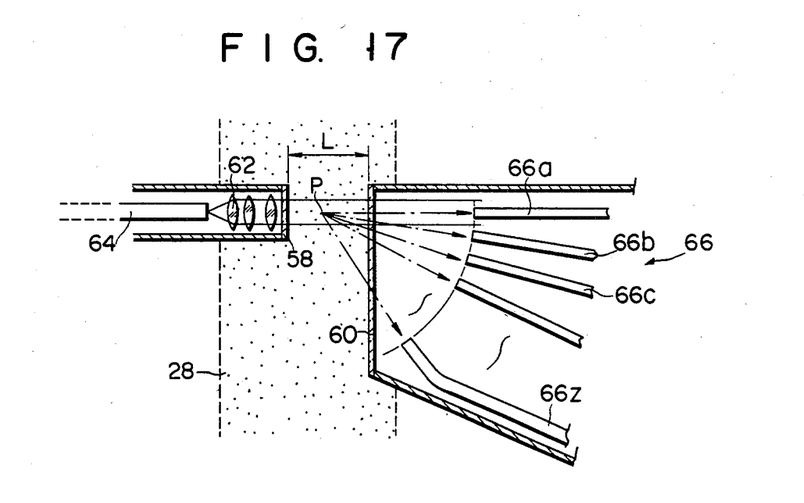
FIG. 17 is a view of another variation of the particle diameter measuring device according to the third embodiment.

In the case of the embodiments shown in FIGS. 10 and 12, the light pass length L is defined by purging air. As shown in FIG. 17, however, the location of the group of particles 28 to be measured may be defined, by glass plates. The glass plate 58 made of glass which allows laser beams to transmit therethrough is so arranged at the front end of the radiating section 54 as to shield the inside of the radiating section 54 from the outside. Another glass plate 60 made of the same glass material is attached to a face of the device body 50 opposite the radiating section 54, so as to shield the hollow inside of the body 50 from the outside. Vapor and liquid drops inside the turbine can be thus prevented from entering the device body 50, radiating section 54 and guide pipe 52, by the glass plates 58, 60.

The angle at which optical fibers are arranged is not limited to 0° to 60°. The optical fibers may be so arranged that this angle is approximately 180°. In this case, the back scattered light can also be measured. To arrange the optical fibers in this manner is advantageous if the fibers cannot be placed in front of the particles for some reason. Further, the optical fibers need not always be arranged so as to have their receiving ends aligned on a straight line. These may be so arranged that their receiving ends are located on a spiral.

What is claimed is:

1. A particle diameter measuring device for measuring the particle diameter distribution in a number of particles to be measured, comprising:
    a means for irradiating laser beams onto the group of particles to be measured;
    a plurality of optical fibers, each receiving scattered light at a predetermined scattering angle in relation to the laser beam incident direction;
    a plurality of photo-detectors, each serving to detect the scattered light guided through each of the optical fibers and convert it into an electric signal;
    a means for obtaining a transmission factor t by dividing the intensity of the transmitted light by the intensity of the incident beams;
    a means for defining the light path length L in which laser beams are scattered by the particles to be measured;
    means for adjusting the light path length L in such a way that the transmission factor t becomes not less than 0.6; and
    an arithmetic unit for calculating the particles diameter distribution in the form of relative values of particle densities, using the detected scattered light indensity at the predetermined scattering angle.

2. A particle diameter measuring device according to claim 1, wherein the optical fibers detect the scattered light at scattering angles which are increased by a certain increment.

3. A particle diameter measuring device according to claim 1, wherein the optical fibers include sparsely arranged optical fibers and densely arranged optical fibers, and the light scattered at scattering angles in the range of a small scattering angle is received by the densely arranged optical fibers, and the light scattered at scattering angles in the range of a large scattering angle is received by the sparsely arranged optical fibers.

4. A particle diameter measuring device according to claim 3, wherein the range of the scattering angle at which the scattered light intensities are to be measured is divided into a plurality of ranges of scattering angles, the scattering angles in each of the divided ranges of scattering angles are increased by a certain increment, and the increment in the divided range of small scattering angles is set to be smaller than that in the divided range of large scattering angles.

5. A particle diameter measuring device according to claim 4, wherein each of the optical fibers has a receiving end which is located on a circle whose center is a point located on the light pass in measured particles, the range of the scattering angle at which the scattered light intensities are to be measured is divided into two ranges, and the receiving ends of the optical fibers are arranged close to one another in two layers in one range of small scattering angles, while they are arranged close to one another in one layer in the other range of large scattering angles.

6. A particle diameter measuring device according to claim 3, wherein the scattering angles are gradually increased.

7. A particle diameter measuring device according to claim 3, wherein the scattering angles at which the scattered light intensities are to be measured are in the range of from 0° to 30°.

8. A particle diameter measuring device according to claim 3, wherein the scattering angles at which the scattered light intensities are to be measured are in the range of from 0° to 60°.

9. A particle diameter measuring device for measuring the particle diameter distribution of a number of particles to be measured, comprising:
   a means for irradiating laser beams onto a group of particles to be measured;
   an optical fiber for transmitted light, receiving a light passing (or transmitting) straight in the laser beam incident direction and passing through the particles;
   a plurality of optical fibers for scattered light, each receiving a light scattered at a predetermined scattering angles in relation to the laser beam incident direction;
   a plurality of photo-detectors, each serving to detect the intensity of transmitted light and the scattered light guided through each of the optical fiber for penetrating beam and optical fibers for scattered light and convert it into an electrical signal;
   a means for calculating a transmission factor t using intensity of transmitted light detected by the photo-detectors;
   a means for defining the light path length L in which laser beams are scattered by the particles to be measured;
   a means for adjusting the light path L in such a way that the transmission factor t becomes not less than 0.6;
   a means for calculating the particle diameter distribution n(D) in the form of relative values of particles densities, using the scattered light intensities at the scattering angles, said light intensities being detected by the photo-dectors; and
   a means for calculating the particle diameter distribution N(D) in the form of absolute values of particles densities, using both the particle diameter distribution n(D) of relative values and the transmission factor t.

10. A particle diameter measuring device according to claim 9, wherein the defining means comprises a first glass plate arranged to shield the radiating means from the outside and allow laser beams to pass therethrough; and a second glass plate, arranged opposite the first glass plate, to shield the optical fibers from the outside and allow laser beams to pass therethrough; the particles to be measured being between the first and second glass plates, and the light pass length L being defined by the distance between these glass plates.

11. A particle diameter measuring device according to claim 10, wherein the radiating means includes a laser beam generator; a radiating optical fiber, one end of which is connected to the laser beam generator to guide a laser beam therethrough; collimator lenses arranged in front of the other end of the radiating optical fiber; and a radiating section which houses the collimator lenses and is capable of reciprocating in conjunction with the collimator along the optical axis of the collimator lenses; with the first glass plate of the defining means being arranged in front of the radiating section and the adjusting means reciprocating the radiating section in such a way as to adjust the light pass length L.

12. A particle diameter measuring device according to claim 9, wherein the optical fibers detect the scattered light at scattering angles which are increased by a certain increment.

13. A particle diameter measuring device according to claim 9, wherein the optical fibers include optical fibers sparsely arranged and optical fibers densely arranged, the light scattered at the scattering angles in the range of a small scattering angle is received by the optical fibers densely arranged, and the light scattered at the scattering angles in the range of a large scattering angle is received by the optical fibers sparsely arranged.

14. A particle diameter measuring device according to claim 13, wherein the range of the scattering angle at which the scattered light intensities are to be measured is divided into a plurality of ranges of scattering angles, the scattering angles in each of the divided ranges of scattering angels are increased by a certain increment, and the increment in the divided range of small scattering angles is set to be smaller than that in the divided range of large scattering angles.

15. A particle diameter measuring device according to claim 14, wherein each of the optical fibers for scattered light has a receiving end which is located on a circle whose center is a point located in the measured particles, the range of the scattering angle at which the scattered light intensities are to be measured is divided into two ranges, and the receiving ends of the optical fibers are arranged close to one another in two layers in one range of small scattering angles, while they are arranged close to one another in one layer in the other range of large scattering angles.

16. A particle diameter measuring device according to claim 14, wherein the scattering angles at which the scattered light intensities are to be measured are in the range of from 0° to 30°.

17. A particle diameter measuring device according to claim 14, wherein the scattering angles at which the scattered light intensities are to be measured are in the range of from 0° to 60°.

18. A particle diameter measuring device according to claim 13, wherein the scattering angles are gradually increased.

* * * * *